(12) United States Patent
Pacetti

(10) Patent No.: US 9,345,597 B2
(45) Date of Patent: May 24, 2016

(54) POLYMERIC STENT WITH STRUCTURAL RADIOPAQUE MARKER

(71) Applicant: Abbott Cardiovascular Systems Inc., Santa Clara, CA (US)

(72) Inventor: Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 125 days.

(21) Appl. No.: 13/937,921

(22) Filed: Jul. 9, 2013

(65) Prior Publication Data

US 2015/0018934 A1    Jan. 15, 2015

(51) Int. Cl.
*A61F 2/06* (2013.01)
*A61F 2/89* (2013.01)
*A61L 31/18* (2006.01)
*A61F 2/915* (2013.01)

(52) U.S. Cl.
CPC . *A61F 2/89* (2013.01); *A61F 2/915* (2013.01); *A61L 31/18* (2013.01); *A61F 2250/0071* (2013.01); *A61F 2250/0098* (2013.01)

(58) Field of Classification Search
CPC ............... A61F 2250/0071; A61F 2250/0098; A61F 2/89; A61F 2/915; A61F 2002/91558; A61F 2002/91591; A61F 2002/91566; A61F 2002/91575

USPC ...................... 623/1.15, 1.16, 1.34
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 5,514,154 A | 5/1996 | Lau et al. | |
| 5,569,295 A | 10/1996 | Lam | |
| 5,741,327 A | 4/1998 | Frantzen | |
| 6,565,599 B1 * | 5/2003 | Hong et al. | 623/1.15 |
| 7,326,239 B1 * | 2/2008 | Fedida | 623/1.15 |
| 7,476,245 B2 | 1/2009 | Abbate | |
| 8,002,817 B2 | 8/2011 | Limon | |
| 8,303,644 B2 | 11/2012 | Lord et al. | |
| 8,388,673 B2 | 3/2013 | Yang et al. | |
| 2003/0195609 A1 * | 10/2003 | Berenstein et al. | 623/1.15 |
| 2004/0127970 A1 | 7/2004 | Saunders et al. | |
| 2009/0024205 A1 * | 1/2009 | Hebert et al. | 623/1.16 |
| 2010/0244305 A1 | 9/2010 | Contiliano et al. | |
| 2013/0085563 A1 | 4/2013 | Stankus et al. | |

* cited by examiner

*Primary Examiner* — Katherine M Shi
(74) *Attorney, Agent, or Firm* — Squire Patton Boggs (US) LLP

(57) ABSTRACT

An implantable sent comprises a radiopaque marker that provides a structural connection between two parts made of a polymer substrate material. The two parts can be one bending element of one radially expandable ring and another bending element of an adjacent expandable ring. The two parts can be two bending elements of the same radially expandable ring. The radiopaque marker can be in the form of an entire radially expandable ring.

9 Claims, 9 Drawing Sheets

POLYMERIC STENT WITH STRUCTURAL RADIOPAQUE MARKER

FIELD OF THE INVENTION

This invention relates generally to implantable medical devices and, more particularly, to polymeric stents.

BACKGROUND OF THE INVENTION

Stents are frequently used in the medical field to open vessels affected by conditions such as stenosis, thrombosis, restenosis, vulnerable plaque, and formation of intimal flaps or torn arterial linings caused by percutaneous transluminal coronary angioplasty (PCTA). Stents are used not only as a mechanical intervention, but also as vehicles for providing biological therapy. As a mechanical intervention, stents act as scaffoldings, functioning to physically hold open and, if desired, to expand a vessel wall. Stents may be capable of being compressed in diameter, so that they can be moved through small vessels with the use of a catheter or balloon-catheter, and then expanded to a larger diameter once they are at the target location. Accurate positioning of the stent at the target location involves the use of fluoroscopy, which relies on the stent being radiopaque to distinguish it from surrounding tissue and from the delivery device, such as a catheter, on which it is being carried. Examples of such stents include those described in U.S. Pat. No. 4,733,665 to Palmaz, U.S. Pat. No. 4,800,882 to Gianturco, U.S. Pat. No. 4,886,062 to Wiktor, U.S. Pat. No. 5,514,154 to Lau et al., and U.S. Pat. No. 5,569,295 to Lam.

A stent must have sufficient radial strength to withstand structural loads, such as radial compressive forces, imposed on the stent as it supports the walls of a vessel or other anatomical lumen. In addition, the stent must possess sufficient flexibility to allow for crimping, deployment, and cyclic loading from surrounding tissue. Also, a sufficiently low profile, that includes diameter and size of struts, is important. As the profile of a stent decreases, the easier is its delivery through an anatomical lumen, and the smaller the disruption in the flow of blood or other bodily fluid.

FIG. 1 shows an end segment of an exemplary stent 10 designed to be crimped onto a catheter and subsequently expanded. Stent 10 has a cylindrical shape having central axis 12 and includes a pattern of interconnecting structural elements or struts 14. Axis 12 extends through the center of the cylindrical shape formed by struts 14. The stresses involved during compression and deployment are generally distributed throughout various struts 14. A surface coating of material may be applied over the struts 14. As opposed to the surface coating of material, it is the underlying structure or substrate material of struts 14 that is typically the primary source of the radial strength of stent 10.

There are different types of struts 14. Struts 14 include a series of ring struts 16 that are connected to each other by bending elements 18. Ring struts 16 and bending elements 18 form rings 20 configured to be reduced and expanded in diameter. Rings 20 are arranged longitudinally and centered on axis 12. Struts 14 also include link struts 22 that connect rings 20 to each other. Rings 20 and link struts 22 collectively form a tubular scaffold of stent 10.

Bending elements 18 bend to a more acute angle when stent 10 is crimped to allow radial compression of stent 10 in preparation for delivery through an anatomical lumen. Bending elements 18 subsequently open to a larger angle when stent 10 is deployed to allow for radial expansion of stent 10 within the anatomical lumen. After deployment, stent 10 is subjected to static and cyclic compressive loads from surrounding tissue. Rings 20 are configured to maintain the expanded state of stent 10 after deployment.

Stents made of bioresorbable polymers have been developed to allow for improved healing of the anatomical lumen. Examples of bioresorbable polymer stents include those described in U.S. Pat. No. 8,002,817 to Limon, U.S. Pat. No. 8,303,644 to Lord, and U.S. Pat. No. 8,388,673 to Yang. Because polymers are generally less radiopaque than conventional metals used for stents, metallic radiopaque markers are attached to parts of the stent to allow for visualization and accurate positioning using fluoroscopy.

FIG. 2 shows two metallic radiopaque markers 30 imbedded side by side in link strut 22 between two rings 20. Radiopaque markers 30 are spheres approximately 240 µm in diameter which have been press-fitted into slightly undersized holes of approximately 230 µm diameter. Substrate material 32 forms the perimeter of the holes and extends continuously from one ring 20 to the adjacent ring 20. It is substrate material 32, not radiopaque markers 30, which maintains the connection between rings 20. Rings 20 would remain directly and structurally connected to each other via link strut 22 even when radiopaque markers 30 are removed from the stent.

FIG. 3 shows a fluoroscopic image of a bioabsorbable polymer stent being deployed in a vessel. Two radiopaque markers are imbedded as shown in FIG. 2 at opposite ends of the stent. The radiopaque markers are 240-µm diameter spheres made of platinum. As these markers are close together, they can appear as a single marker depending on the resolution of the fluoroscope. The stent is carried on a balloon catheter which has its own radiopaque markers which demark the edges of the stent or working length of the balloon. The dark spots corresponding to the radiopaque markers on the stent are not as visible as the radiopaque markers on the balloon. The radiopaque markers on the balloon were more visible because they were larger than those on the stent. After the balloon is withdrawn, all that remains visible under fluoroscopy of the bioresorbable stent are the radiopaque markers. For a skilled interventionalist, this can be adequate for locating the bioresorbable stent. However, with patients of larger mass (longer x-ray path length), suboptimal fluoroscopy equipment, or a physician less experienced with the bioresorbable stent, locating the bioresorbable stent can be challenging.

One approach to making the stent more visible is to increase the number of radiopaque markers. As can be imagined from FIG. 3, imbedding more 240 µm markers in line along a thin stent strut will increase the number of faint spots, as opposed to creating a single dark spot that is easily distinguished from its surroundings. Accordingly, this approach is likely to provide little improvement in distinguishing the radiopaque markers on the stent from surrounding structures and from the substantially larger radiopaque markers on the balloon.

Accordingly, there is a continuing need for making polymer structures of a stent more radiopaque without impacting the ability of the bioresorbable stent to meet the mechanical and functional requirements discussed above.

SUMMARY OF THE INVENTION

Briefly and in general terms, the present invention is directed to an implantable stent. In aspects of the present invention, an implantable stent comprises a first ring and a second ring, each of which is configured to radially expand and is made of a polymer substrate material. The stent further comprises a radiopaque marker made of a material having a radiopacity greater than that of the polymer substrate material, wherein the radiopaque marker either connects two ends of the first ring such that elimination of the radiopaque marker results in loss of all direct structural connection between the two ends or connects a first portion of the first ring to a second portion of the second ring such that elimination of the radiopaque marker results in loss of all direct structural connection between the first portion and the second portion.

In aspects of the present invention, an implantable stent comprises a first ring and a second ring, each of which is configured to radially expand and is made of a polymer substrate material. The stent further comprises a link strut connecting the first ring to the second ring, the link strut including a radiopaque marker, wherein no polymer substrate material of the first ring and no polymer substrate material of the second ring extends entirely around and in contact with the radiopaque marker.

In aspects of the present invention, an implantable stent comprises a polymer ring configured to radially expand, the polymer ring made of a polymer substrate material. The stent further comprises a radiopaque marker ring configured to radially expand, the radiopaque marker ring attached to the polymer ring and made of a material having a radiopacity greater than that of the polymer substrate material. The stent further comprises a link strut connecting the polymer ring to the radiopaque marker ring.

The features and advantages of the invention will be more readily understood from the following detailed description which should be read in conjunction with the accompanying drawings.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 6-10A are plan views of a portion of a stent in an un-crimped state, showing radiopaque markers of a link strut.

DETAILED DESCRIPTION OF EXEMPLARY EMBODIMENTS

Figure 1:
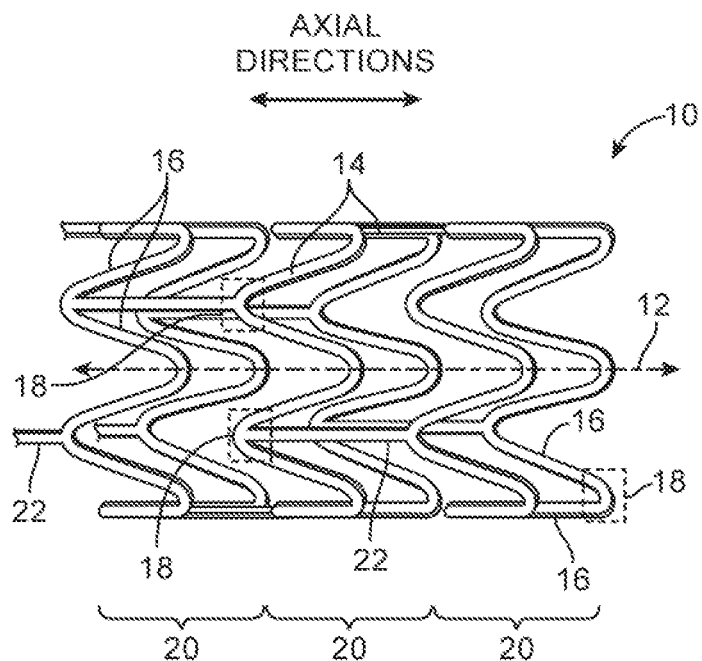
FIG. 1 is a perspective view of a prior art stent.

As used herein, a "stent" is a device that is placed inside the body of a person or animal and, more particularly, within an anatomical lumen or cavity. Examples of lumen and cavities in which a stent can be placed include without limitation arterial or venous vasculature, urethra, ureter, fallopian tubes, esophagus, and the like. Non-limiting examples of stents within the scope of the present invention are those which are non-expanding, self-expanding, and balloon expandable, and which are configured for non-percutaneous delivery methods and configured for percutaneous transluminal delivery methods. Stents which are comprised of bioresorbable, bioabsorbable, biodegradable, or bioerodible materials are sometimes referred to as scaffolds due to their temporary nature.

As used herein, "bioresorbable" refers to a material capable being completely eroded, degraded (either biodegraded and/or chemically degraded), and/or absorbed when exposed to bodily fluids (such as blood or other fluid); and can be gradually resorbed, absorbed and/or eliminated by the body.

As used herein, "biostable" refers to a material that is not bioresorbable.

As used herein, "radiopacity" refers to the relative inability of electromagnetic radiation, particularly X-rays, to pass through a particular material.

As used herein, "abluminal surface" refers to a radially outward facing surface.

As used herein, "luminal surface" refers to a radially inward facing surface.

As used herein, "bulb" and "knob" are interchangeable and refer to a portion of a structure joined by a neck to another portion of the structure.

As used herein, "cavity" and "recess" are interchangeable and refer to a hole in a structure.

As used herein, "comprising" and "including" are interchangeable with each other, are inclusive or open-ended and do not exclude additional, unrecited elements. In contrast, the phrases "consists of" and "consisting of" exclude any element or type of ingredient not specified.

As used herein, "consists essentially of" and "consisting essentially of" mean that the subject structure includes the recited items and optionally includes unspecified items that do not materially affect the basic characteristics provided to the structure by the recited items.

As used herein, a reference numeral with a letter (such as "a" or "b") refers to an element of a group. A description using the same reference numeral without letters refers to members of the group. For example, the phrase "rings 20" in plural form is equivalent to the phrase "rings 20a and 20b"; the phrase "each ring 20" in singular form is equivalent to the phrase "each of rings 20a and 20b"; and the phrase "respective ring 20" is equivalent to the phrase "ring 20a or 20b, respectively"

Figure 4A:
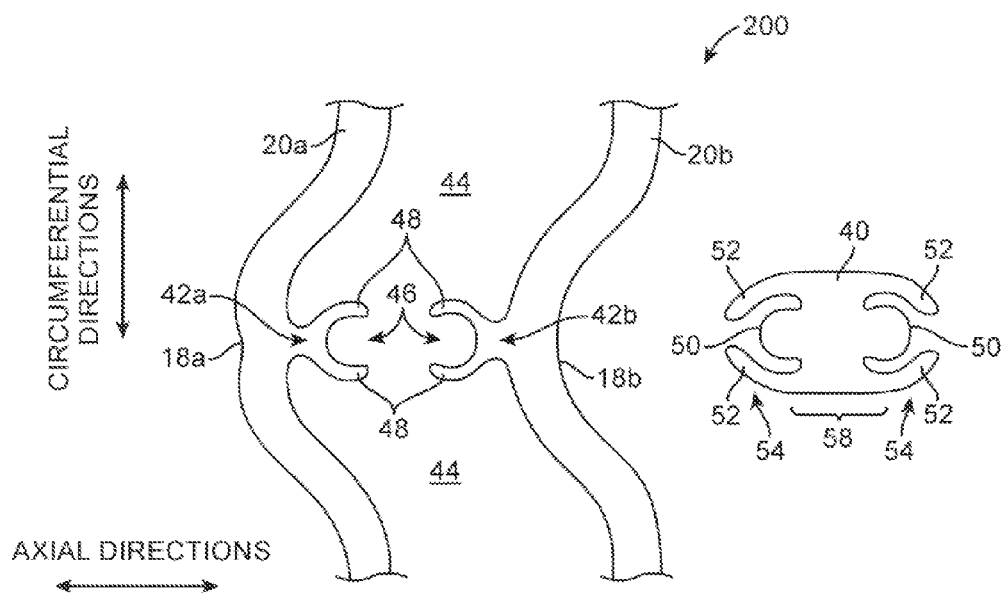
FIGS. 4A and 4B are plan views of a portion of a stent in an un-crimped state, showing a radiopaque marker of a link strut.
Figure 4B:
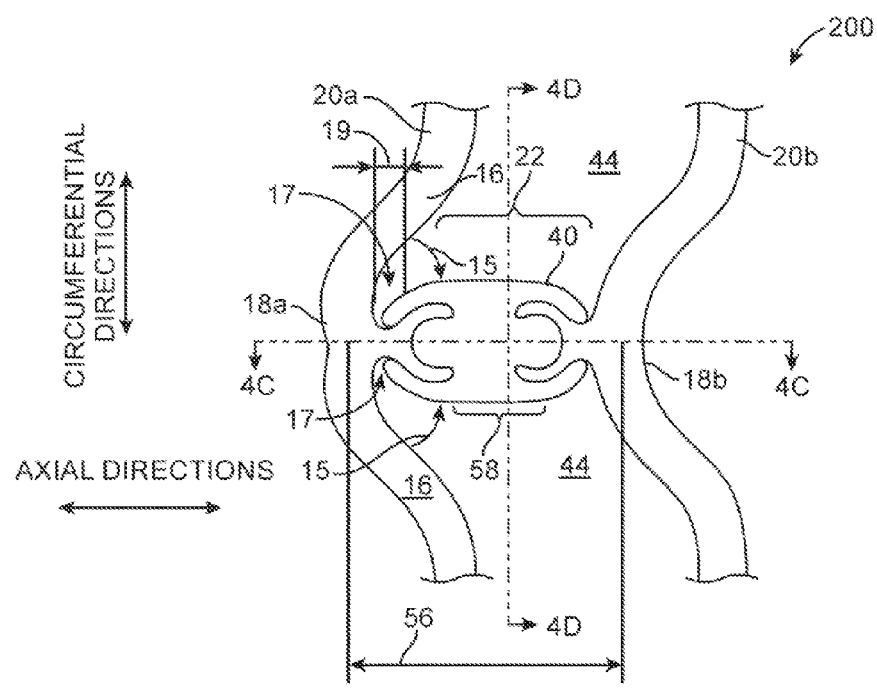

Referring now in more detail to the exemplary drawings for purposes of illustrating embodiments of the invention, wherein like reference numerals designate corresponding or like elements among the several views, there is shown in FIGS. 4A-4D a portion of an exemplary stent 200 comprising rings 20 and link strut 22. Rings 20 are connected to each other by link strut 22 (FIG. 4B). Link strut 22 includes radiopaque marker 40 and a pair of retainers 42 that protrude from bending elements 18 of rings 20.

FIG. 4A shows radiopaque marker 40 separated from the remainder of stent 200. Radiopaque marker 40 is not shaped as a sphere and is elongate with opposite ends 54. Retainer 42a (first retainer) and retainer 42b (second retainer) protrude into open space 44 between rings 20a and 20b. Retainer 42a protrudes in a direction toward ring 20b. Retainer 42b protrudes in a direction toward ring 20a. Each retainer 42 is integrally formed on respective ring 20. Integrally formed means that each retainer 42 is made of the same polymer substrate material as the ring to which it is attached and there is no adhesive and no intervening structure required to attach that retainer to its respective ring. Cavities 46 of retainers 42 face toward each other. Each cavity 46 is disposed between fingers 48. Fingers 48 of retainer 42a do not contact fingers 48 of retainer 42b.

As shown in FIG. 4B, each retainer 42 is configured to mate with and engage respective bulb 50 and fingers 52 at opposite ends 54 of radiopaque marker 40. Each bulb 50 is disposed between two fingers 52. Radiopaque marker 40 is retained by interdigitation of fingers 48 into the space between bulb 50 and fingers 52 of radiopaque marker 40. Each cavity 46 of retainers 42 is configured to receive and mate with a respective bulb 50. Cavities 46 function to maximize the amount of radiopaque material within link strut 22. Fingers 48 interlock with fingers 52 to prevent rings 20 from separating and to maintain axial distance 56 between bending elements 18 during crimping (reduction in diameter) and expansion (increase in diameter) of rings 20 in circumferential directions. Distance 56 is maintained when radiopaque marker 40 is under tension and compression in the axial direction.

Radiopaque marker 40 is arranged relative to ring 20a (first ring) in such a way to facilitate movement of ring struts 16 of ring 20a toward link strut 22. During crimping of ring 20a, bending element 18a flexes to allow adjoining struts 16 to move in the direction of arrows 15. The closer struts 16 are able to move toward each other, the smaller the diameter to which ring 20a can be crimped. FIG. 4B shows the stent in an un-crimped state before it is crimped. In the un-crimped state, empty axial spaces 17 exist between end 54 of radiopaque marker 40 and adjacent ring strut 16. Empty axial spaces 17 allow adjacent ring struts 16 to move in the direction of arrows 15 without interference or with minimal interference from radiopaque marker 40. Empty axial spaces 17 are defined by an axial distance 19 which separates radiopaque marker 40 from adjacent ring 20a. As used herein, an axial distance runs in an axial direction parallel to the central axis of a stent. After crimping of ring 20a to a crimped state, axial distance 19 is reduced or eliminated entirely.

Radiopaque marker 40 is arranged such that its elimination or removal (as shown in FIG. 4A) would result in loss of all direct structural connection between axially adjacent bending element 18a (a first portion of first ring 20a) and bending element 18b (a second portion of second ring 20a). With the loss of all direct structural connection, adjacent bending elements 18a and 18b may still be connected indirectly to each other by another link strut. For example, rings 20a and 20b can be connected to each other by link strut 22 (a first link strut) and a second link strut. Elimination of radiopaque marker 40 from link strut 22 (the first link strut) would result in a loss of all direct structural connection but would not result in loss of indirect structural connection provided by the second link strut.

Elimination of radiopaque marker 40 would result in a complete structural break in the link strut 22 from which it is removed. A complete structural break would occur even if a surface coating were present over rings 20 and radiopaque marker 40, because the surface coating would be removed due to adhesion to radiopaque marker 40 and because the surface coating could not withstand forces imposed on the stent when implanted.

Figure 2:
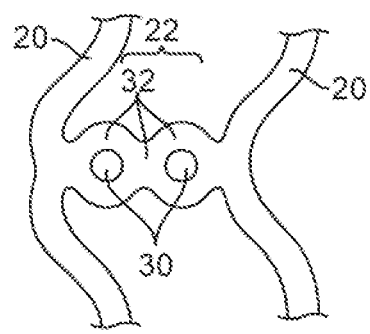
FIG. 2 is a plan view of prior art radiopaque markers imbedded in a link strut.

As compared to FIG. 2, elimination of prior art radiopaque marker 30 does not result in a complete structural break in link strut 22. Link strut 22 would have two empty holes but continuity in structural connection is maintained by substrate material 32 between the rings even with the elimination of radiopaque marker 30 from the link strut.

Figure 4C:
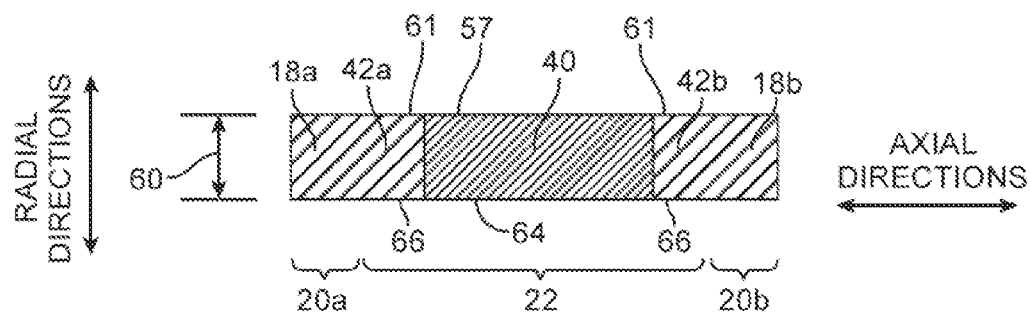
FIGS. 4C and 4D are cross-sectional views along lines 4C-4C and 4D-4D in FIG. 4B, showing the radial thickness of the radiopaque marker in relation to other parts of the stent.

As shown in FIG. 4C, link strut 22 has a uniform radial thickness across the entire axial length of link strut 22. As used herein, the radial thickness of a particular part is the maximum dimension of that part measured in a radial direction perpendicular to the central axis (for example, axis 16 in FIG. 1) of a stent. The axial length of a particular feature is the maximum dimension of that feature in an axial direction parallel to the central axis of the stent. Retainer 42a, radiopaque marker 40, and retainer 42b have the same radial thickness 60. Retainers 42 of link strut 22 and bending elements 18 of rings 20 have the same radial thickness 60. Having the same radial thickness among various parts of the stent can minimize disruption in the flow of blood or other bodily fluid through the stent.

In other embodiments, the radial thickness of radiopaque marker 40 is less than or the same as any one or more of retainer 42a, retainer 42b, bending element 18a, and bending element 18b.

In other embodiments, the radial thickness of radiopaque marker 40 is greater than any one or more of retainer 42a, retainer 42b, bending element 18a, and bending element 18b.

Referring again to FIG. 4C, abluminal surface 57 of radiopaque marker 40 is even with abluminal surface 61 of retainers 42 and bending elements 18. Abluminal surface 57 is axially in line with abluminal surface 61. Luminal surface 64 of radiopaque marker 40 is even with luminal surface 66 of retainers 42 and bending elements 18. Luminal surface 64 is axially in line with luminal surface 66.

Figure 4D:
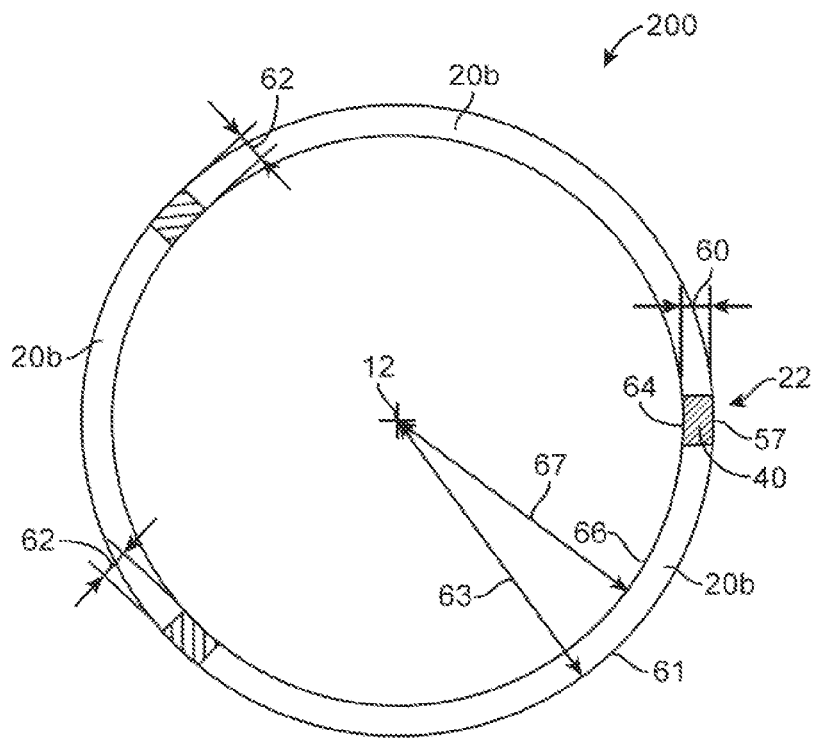

FIG. 4D is a cross section of stent 200 with the section intersecting three radiopaque links 40 and the rest of the stent shown in projection. As shown in FIG. 4D, radiopaque marker 40 has radial thickness 60 that is the same as radial thickness 62 of link struts that have no radiopaque marker. Radiopaque marker 40 has the same radial thickness as other parts of adjacent ring 20b. Radiopaque marker 40 can have the same radial thickness as all rings of the stent. As mentioned above, having the same radial thickness among various parts of the stent can minimize disruption in the flow of blood or other bodily fluid through the stent.

In alternative embodiments, radial thickness 60 of radiopaque marker 40 is less than any of: (1) radial thickness 62 of link struts that have no radiopaque marker, (2) the radial thickness of rings struts of ring 20b adjacent to radiopaque marker 40, and (3) the radial thickness of all rings of the stent.

In alternative embodiments, radial thickness 60 of radiopaque marker 40 is greater than any of: (1) radial thickness 62 of link struts that have no radiopaque marker, (2) the radial thickness of rings struts of ring 20b adjacent to radiopaque marker 40, and (3) the radial thickness of all rings of the stent.

Referring again to FIG. 4D, abluminal surface 57 of radiopaque marker 40 and abluminal surface 61 of adjacent ring 20b are at the same radial distance 63 from central axis 12 of stent 200. Luminal surface 64 of radiopaque marker 40 and luminal surface 66 of adjacent ring 20b are at the same radial distance 67 from central axis 12.

Radiopaque marker 40 shown in FIGS. 4A-4D can be implemented for any link strut located anywhere in a stent strut pattern. Radiopaque marker 40 of FIGS. 4A-4D can be implemented on any number of different stent strut patterns for a polymer stent, such as the stent strut patterns described in U.S. Pat. No. 8,002,817, No. 8,303,644, and No. 8,388,673, and in U.S. Publication Nos. 2010/0244305 and 2013/0085563. There is no limit on the stent strut pattern which can incorporate radiopaque marker 40.

Figure 5:
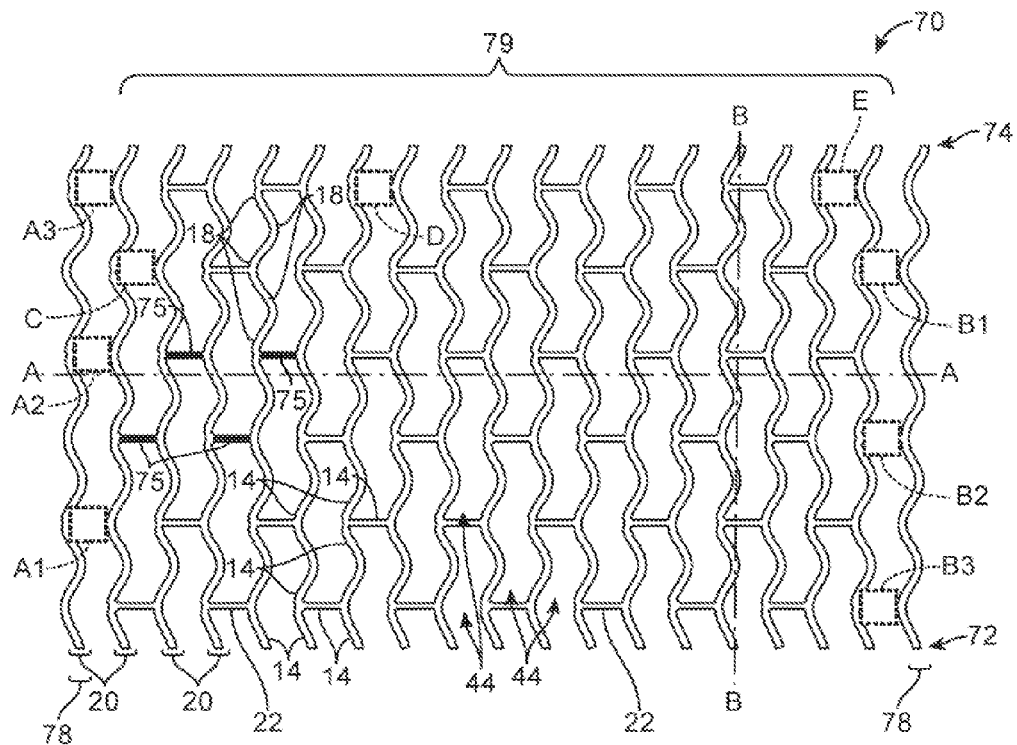
FIG. 5 is a flattened, plan view of a stent strut pattern, showing non-limiting examples of where radiopaque markers can be located.

FIG. 5 shows exemplary stent strut pattern 70 of stent 200. Line A-A runs in an axial direction. Line B-B runs in a circumferential direction. Stent pattern 70 is shown in a planar or flattened view for ease of illustration and clarity, although stent pattern 70 actually extends around the stent so that line A-A is parallel or substantially parallel to the central axis of the stent. Pattern 70 is illustrated with bottom edge 72 and top edge 74. On a stent, bottom edge 72 meets top edge 74 so that line B-B forms a circle around the stent. Stent pattern 70 includes various struts 14 oriented in different directions and open spaces 44 between rings 20. Rings 20 are connected to each other by another by link struts 22 that have individual lengthwise axes 75 parallel to line A-A and the central axis of the stent. Each ring 20 is capable of being radially collapsed to a smaller diameter during crimping and then radially expanded to a deployed diameter. The deployed diameter can be less than, the same as, or greater than the original diameter of ring 20 prior to crimping.

Either ring 20a or ring 20b of FIGS. 4A-4D can be end ring 78 in FIG. 5 at either end of the stent. For example, radiopaque marker 40 can be implemented for a link strut at location A1 and B1. Two or more radiopaque markers 40 can be implemented at the ends of the stent. For example, one radiopaque marker 40 can be implemented for a link strut at each of locations A1, A2, A3, B1, B2 and B3. In other instances, ring 20a and ring 20b are not end rings, and they can be located in middle segment 79 of the stent. For example, radiopaque marker 40 can be implemented for a link strut at any of locations C, D and E.

Figure 6:
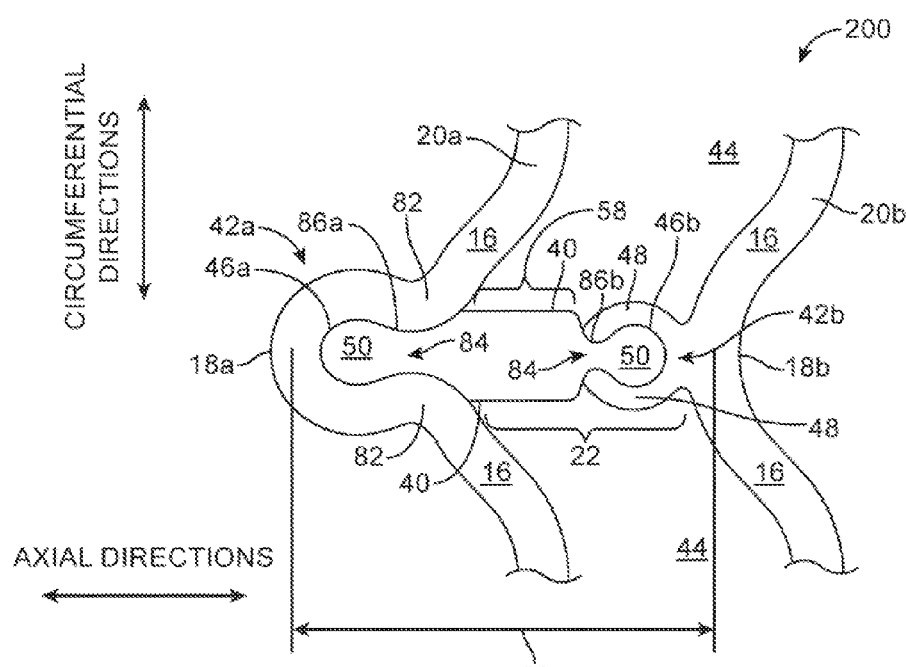
Figure 7:
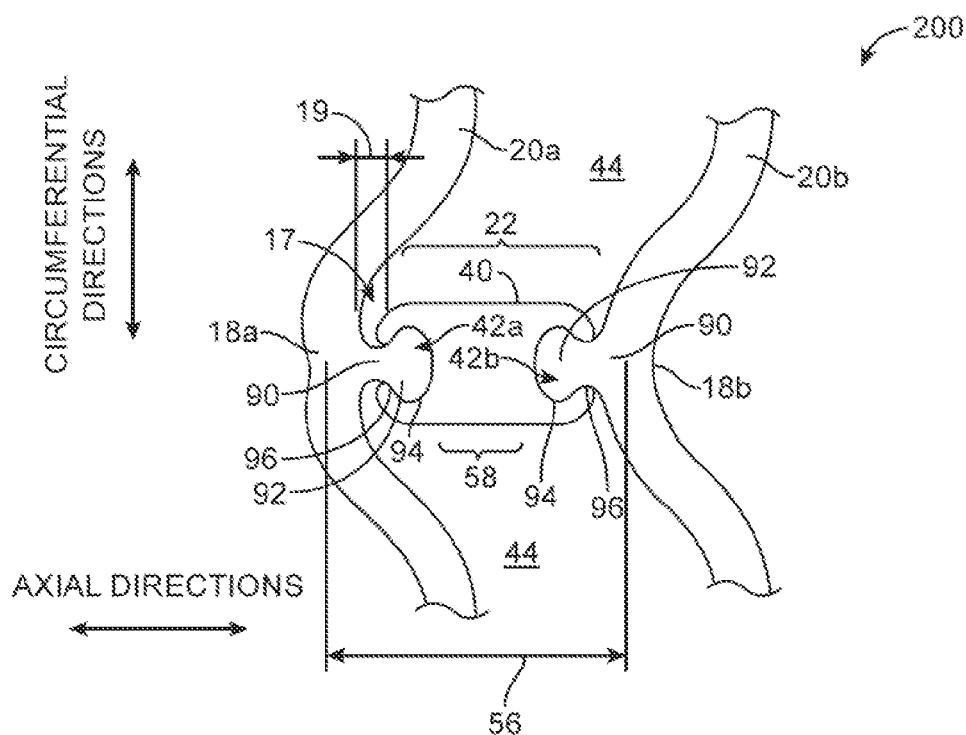
Figure 8:
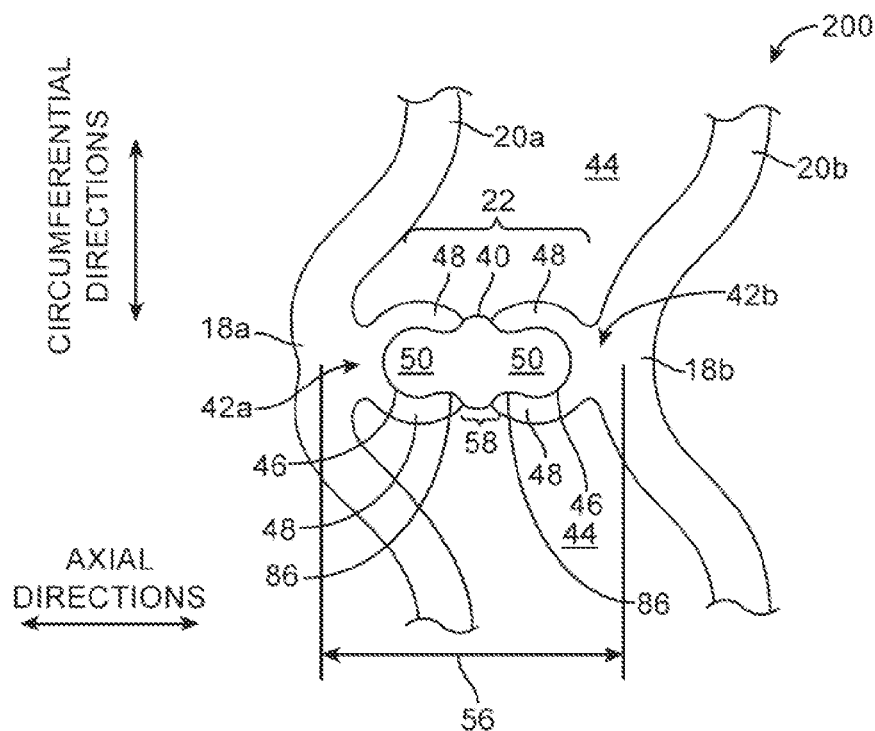
Figure 9:
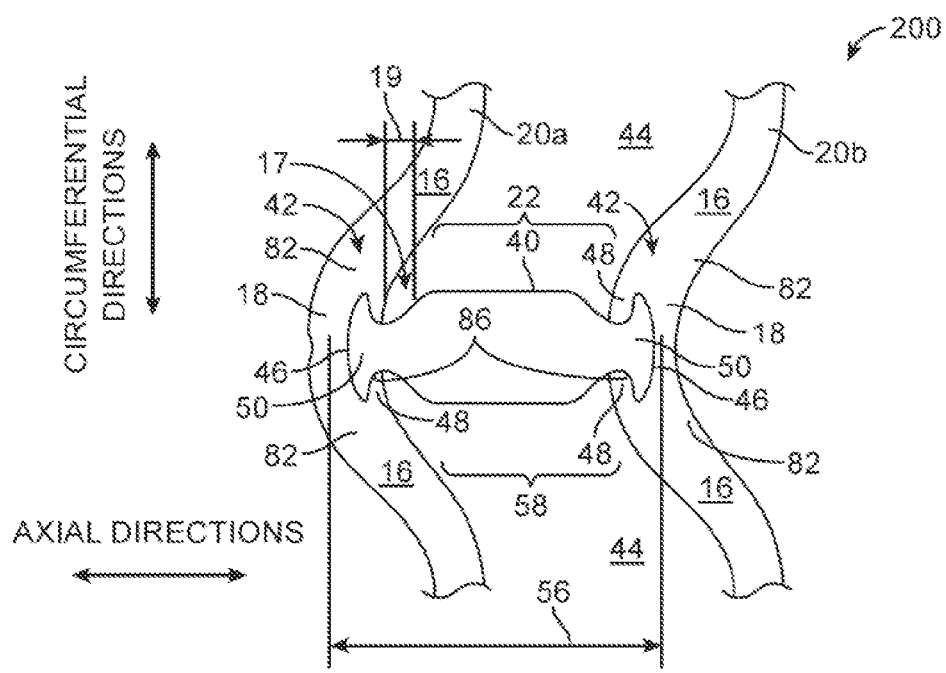

FIGS. 6-10D show various configurations of link strut 22 in a portion of exemplary stent 200. Two rings 20 are connected to each other by link strut 22 which serve the same purpose as link strut 22 in FIGS. 4A-4D. Retainers 42 on rings 20 are configured to mate with and engage radiopaque marker 40 of link strut 22. The engagement prevents relative motion in axial directions between retainers 42 and radiopaque marker 40 during crimping and expansion of rings 20. With radiopaque marker 40 retained in link strut 22, axial distance 56 between bending elements 18 of rings 20 is maintained during crimping and expansion of rings 20. In FIGS. 7 and 9, empty axial spaces 17, each having axial distance 19, serve the same purpose as those described for FIG. 4B.

In FIGS. 6-9, radiopaque marker 40 is arranged such that its elimination would result in loss of all direct structural connection between axially adjacent bending elements 18. Also, elimination of radiopaque marker 40 would result in a complete structural break in the link strut 22 from which it is eliminated. It is to be understood that loss of all direct structural connection does necessarily mean the loss of all structural connection. As shown in FIG. 5, two rings can be connected to each other via multiple link struts. Therefore, even with the loss of all direct structural connection between particular parts of the rings in the vicinity of a first link strut due to elimination of a radiopaque marker from the first link strut, the parts of the rings in the vicinity of a first link can still be connected indirectly via other link struts.

The descriptions given above for possible locations and numerical quantity of link strut 22 of FIGS. 4A-4D can be applied to link strut 22 of FIGS. 6-10D to form various embodiments.

The descriptions for radial thickness, abluminal surface, and luminal surface of radiopaque marker 40 in FIGS. 4C and 4D can be applied to radiopaque marker 40 in FIGS. 6-9 to form various embodiments.

In FIG. 6, link strut 22 includes radiopaque marker 40 and retainer 42b on ring 20b. Retainer 42a protrudes away from open space 44 between rings 20a and 20b. Retainer 42a protrudes in a direction away from ring 20b. Retainer 42b protrudes into open space 44. Retainer 42b protrudes in a direction toward ring 20a. Each retainer 42 is integrally formed on respective ring 20. Cavities 46 of retainers 42 face toward each other. Cavity 46a is defined by ends 82 of two ring struts 16 of ring 20a. Ends 82 are joined together by bending element 18a which protrudes away from open space 44 between ring 20a and ring 20b. Bending element 18a forms the side walls and base of cavity 46a, the base being located opposite cavity inlet 86a. Cavity 46b is disposed between fingers 48 that protrude into open space 44. Bending element 18b forms the base of cavity 46b located opposite cavity inlet 86b.

Each retainer 42 is configured to mate with and engage respective bulb 50. Each bulb 50 includes neck 84 which fits in respective cavity inlet 86. Each cavity 46 is configured to receive and mate with respective bulb 50. Radiopaque marker 40 is retained by entrapment of bulbs 50 within cavities 46. Cavity inlets 86 are smaller in circumferential width than bulbs 50, which enables bulbs 50 to remain trapped within cavities 46 during crimping and expansion of rings 20. As used herein, the circumferential width of a structural feature is the maximum dimension of that feature measured in a circumferential direction.

In FIG. 7, link strut 22 includes radiopaque marker 40, retainer 42a on ring 20a, and retainer 42b on ring 20b. Retainers 42 protrude into open space 44 between rings 20. Retainer 42a protrudes in a direction toward ring 20b. Retainer 42b protrudes in a direction toward ring 20a. Each Retainer 42 is integrally formed on respective ring 20. Each retainer 42 includes neck 90 and knob 92. Neck 90 is smaller in circumferential width than knob 92. Neck 90 joins knob 92 to respective bending element 18 of ring 20. Each end of radiopaque marker 40 includes a C-shaped socket having recess 94 configured to engage and receive knob 92. Recess 94 has recess inlet 96 configured to receive neck 90. Radiopaque marker 40 is retained by entrapment of knobs 92 within recesses 94. Each recess inlet 96 is smaller in circumferential width than respective knob 92, which enables knobs 92 to remain trapped within recesses 92 during crimping and expansion of rings 20.

In FIG. 7, each knob 92 is integrally formed on respective rings 20. Thus, the polymer substrate material of rings 20 extends partially through radiopaque marker 40. The polymer substrate material does not extend entirely through radiopaque marker 40 due to the fact that the polymer substrate extends through recesses 94 but does not extend through medial segment 58.

In FIG. 8, link strut 22 includes radiopaque marker 40, retainer 42a on ring 20a, and retainer 42b on ring 20b. Bulbs 50 are formed at opposite ends of radiopaque marker 40. Retainers 42 protrude into open space 44 between rings 20. Retainer 42a protrudes in a direction toward ring 20b.

Retainer 42b protrudes in a direction toward ring 20a. Each retainer 42 is integrally formed on respective ring 20. Each retainer 42 is in the form of a C-shaped socket having cavity 46 between hooked fingers 48. Each cavity inlet 86 is smaller in circumferential width than respective cavity 46, which is configured to receive and engage bulb 50. Radiopaque marker 40 is retained by entrapment of bulbs 50 within cavities 46. Each cavity inlet 86 is smaller in circumferential width than respective bulb 50, which enables bulbs 50 to remain trapped within cavities 46 during crimping and expansion of rings 20.

In FIG. 8, each pair of hooked fingers 48 is integrally formed on respective rings 20. Thus, the polymer substrate material of rings 20 extend partially around radiopaque marker 40. The polymer substrate material does not extend entirely around and in contact with radiopaque marker 40 due to the fact that the polymer substrate material extends around and adjacent to bulbs 20 but does not extend around and in contact with medial segment 58.

In FIG. 9, link strut 22 includes radiopaque marker 40. Bulbs 50 are integrally formed at opposite ends of radiopaque marker 40. Radiopaque marker 40 is held in place by retainers 42 contained entirely within the outline of bending elements 18 that join ends 82 of ring struts 16. Retainers 42 do not protrude into open space 44 between rings 20. Having retainers 42 contained entirely within bending elements 18 maximizes the amount of radiopaque material within link strut 22. Each retainer 42 is in the form of a C-shaped socket having cavity 46 between hooked fingers 48. Cavity inlets 86 are smaller in circumferential width than cavities 46, which are configured to receive and engage bulbs 50. Radiopaque marker 40 is retained by entrapment of bulbs 50 within cavities 46. Each cavity inlet 86 is smaller in circumferential width than respective bulb 50, which enables bulbs 50 to remain trapped within cavities 46 during crimping and expansion of rings 20.

In FIGS. 4A-4D and 6-9, radiopaque marker 40 includes medial segment 58 between the opposite ends of radiopaque marker 40. No substrate material of either ring 20 extends entirely through or entirely around medial segment 58. A surface coating of material may be applied on top of rings 20 and radiopaque marker 40. Such a coating is not a substrate material of rings 20.

By comparison, in FIG. 2, substrate material 32 of rings 20 extends entirely around radiopaque markers 30. Substrate material 32 extends entire entirely around via a route contacts radiopaque markers 30 and which runs from one ring to the next ring.

In the plan views of FIGS. 4B and 6-9, radiopaque marker 40 divides open space 44 between rings 20. Open space 44 circumferentially above radiopaque marker 40 would merge with open space 44 circumferentially below radiopaque marker 40 if radiopaque marker 40 is eliminated. Radiopaque marker 40 is arranged such that its elimination would result in loss of all direct structural connection between circumferentially adjacent bending elements 18. With radiopaque marker 40 eliminated, it is unlikely that distance 56 would be maintained during crimping and expansion of rings 20.

FIGS. 4A-4D and 6-9 show various forms of retainers 42 for holding radiopaque marker 40 that can be combined to form other embodiments. For example, first ring 20a can have any one of retainers 42 in FIGS. 4A-4D and 6-9 and second ring 20b can have another one of retainers 42 in FIGS. 4A-4D and 6-9.

In FIGS. 10A-10D, link strut 22 includes retainer 42a, retainer 42b, strip 90 of polymer substrate material, and radiopaque marker 100. Strip 90 joins retainers 42 together and extends entirely through the center of radiopaque marker 100. Strip 90 does not extend around radiopaque marker 100. Retainers 42 and strip 90 are integrally formed on rings 20. Radiopaque marker 100 is in the shape of a tube that surrounds strip 90. Each retainer 42 includes flared portion 102 which is greater in circumferential width than strip 90. Neither flared portion 102a nor 102b extends around radiopaque marker 100. Radiopaque marker 100 is trapped between flared portion 102a and flared portion 102b, each of which prevents radiopaque marker 100 from sliding in axial directions along strip 90. Each flared portion 102 is less than or equal to in circumferential width to radiopaque marker 100 and is configured to transfer axial compressive forces $F_C$ to radiopaque marker 100. As opposed to strip 90, it is radiopaque marker 100 that bears most of compressive forces $F_C$, which allows strip 90 to be thinner in plan view than ring struts 16 and link struts which have no radiopaque marker. Having thinner strip 90 allows link strut 22 to have more radiopaque material.

Figure 10A:
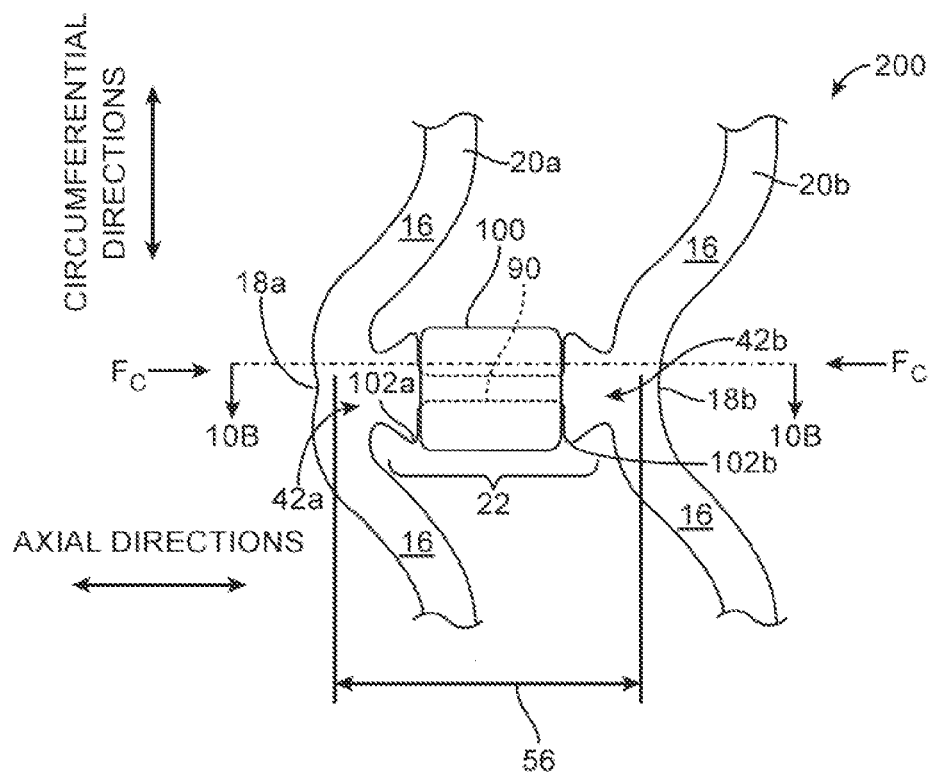
Figure 10B:
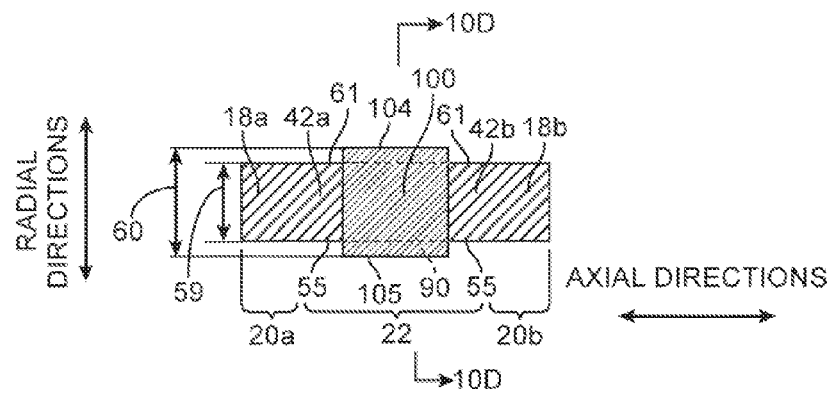
FIG. 10B is a cross-sectional view along line 10B-10B in FIG. 10A, showing the radial thickness of the radiopaque marker in relation to other parts of the stent.

As shown in FIG. 10B, bending elements 18, retainers 42, and strip 90 have the same radial thickness 59, which is less than radial thickness 60 of radiopaque marker 100. Abluminal surface 104 of radiopaque marker 100 protrudes from abluminal surface 61 of retainers 42. Luminal surface 105 of radiopaque marker 100 protrudes from luminal surface 55 of retainers 42.

Having the same radial thickness for bending elements 18, retainers 42, and strip 90 can make it easier to manufacture the stent. Optionally, strip 90 can have a radial thickness that is less than that of retainers 42 so that radiopaque marker 100 does not protrude from the remainder of the stent. For example, strip 90 can have a radial thickness that is less than that of retainers 42 so that: (1) abluminal surface 104 of radiopaque marker 100 is even with and is axially in line with abluminal surface 61 of retainers 42; and/or (2) luminal surface 105 of radiopaque marker 100 is even with and is axially in line with luminal surface 55 of retainers 42.

As indicated above, radiopaque marker 100 surrounds strip 90. In some embodiments, the wall thickness of radiopaque marker 100 is uniform around strip 90. In alternative embodiments, the wall thickness of radiopaque marker 100 is not uniform, as shown in FIGS. 10C and 10D.

Figures 10C, 10D:
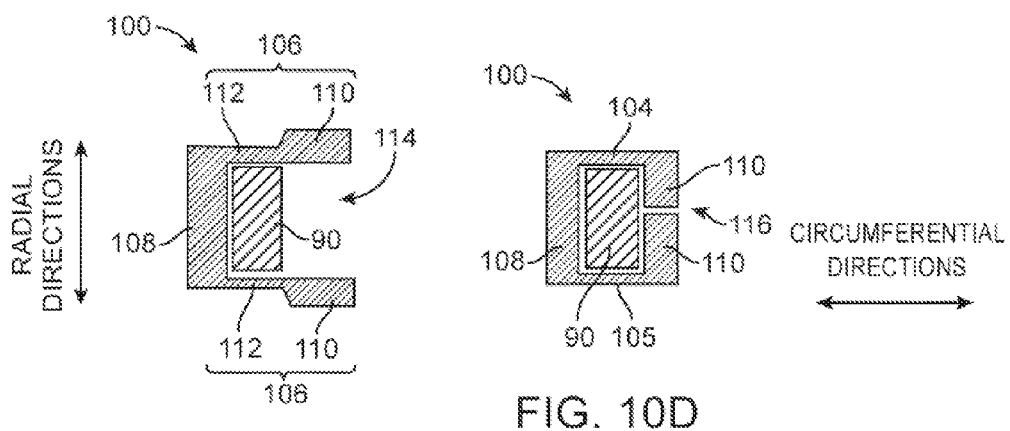
FIG. 10C is a cross-sectional view showing the radiopaque marker of FIG. 10A while in an open state.
FIG. 10D is a cross-sectional view along line 10D-10D in FIG. 10B, showing the radiopaque marker in a closed state.

Referring to FIGS. 10C and 10D, radiopaque marker 100 includes two arms 106 and base 108 which join arms 106 together. Each arm 106 includes upper segment 110 and lower segment 112 connected to base 108. Base 108 and upper segments 110 are located on circumferentially facing sides of strip 90 after the marker 100 is crimped in place. Lower segments 112 are located on radially outward and inward facing sides of strip 90. The wall thicknesses of base 108 and upper segments 110 are greater than the wall thicknesses of lower segments 112. It is the wall thicknesses of lower segments 112 that protrude from the polymer substrate material of strip 90, retainers 42, and bending elements 18 in FIG. 10B. Having thinner wall thicknesses for lower segments 112 minimizes the extent to which radiopaque marker 100 protrudes from the polymer substrate material.

FIGS. 10C and 10D show a process for mounting radiopaque marker 100 on a stent. First, as shown in FIG. 10C, radiopaque marker 100 is placed over strip 90 while radiopaque marker 100 is in an open state. Strip 90 was passed through opening 114 between arms 106. Next, as shown in FIG. 10D, arms 106 are deformed so that upper segments 110 are bent toward each other and so that opening 114 is reduced in size to become narrow seam 116 through which strip 90 is unable to pass. A crimping tool can be used to bend arms 106 without damaging strip 90.

In FIG. 10D, radiopaque marker 100 is in a closed state and fixed around strip 90. Seam 116 is open in that ends of upper segments 110 do not meet or partially meet. In alternative embodiments, seam 116 is closed by contact between ends of upper segments 110 and/or material filled into seam 116.

Radiopaque marker 100 is oriented on strip 90 such that lower segments 112 form abluminal surface 104 and luminal surface 105 of radiopaque marker 100. Base 108 and upper segments 110 form side surfaces which face in circumferential directions. As such, seam 116 does not face radially outward toward surrounding tissue or face radially inward toward flow of blood or other body fluid through the center of the stent. Thus, seam 116 has minimal impact on surrounding tissue after implantation.

In alternative embodiments, radiopaque marker 100 is oriented on strip 90 such that seam 116 is on relatively thin segment 112 at abluminal surface 104. Thus, seam 116 has no impact on fluid flow through the stent after implantation.

The non-uniform wall thickness of radiopaque marker 100 enables minimization of the extent to which it protrudes from the polymer substrate material of the stent and enables maximization of the amount of radiopaque material. The non-uniform wall thicknesses of radiopaque marker 100 can be fabricated by a process of stamping followed by laser cutting. A flat sheet of radiopaque material can be stamped to form the cross-sectional shape shown in FIG. 10C. Next, the stamped material can be cut by a laser to produce multiple radiopaque markers 100, each having an axial length that fits between flared portions 102 (FIG. 10A).

Figure 11:
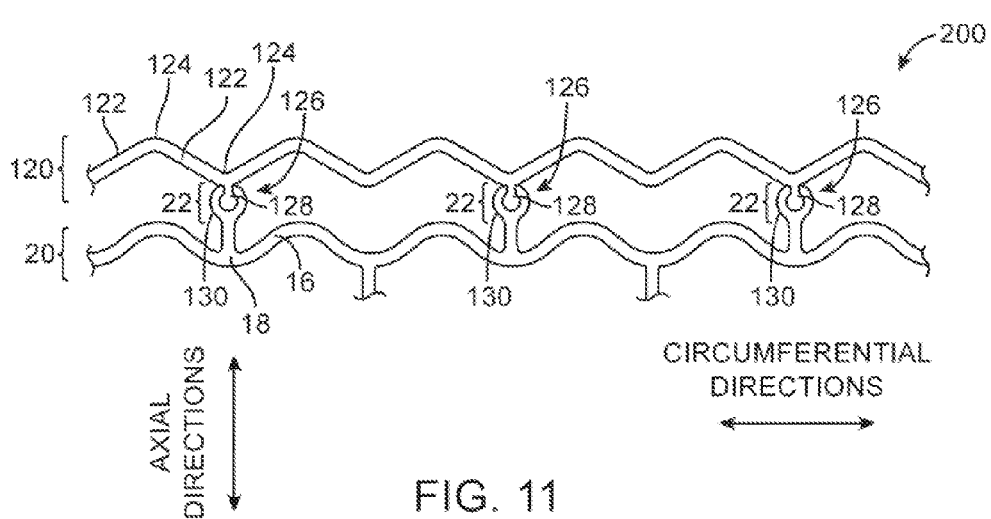
FIG. 11 is a flattened, plan view of a portion of a stent in an un-crimped state, showing a radiopaque marker in the form of a radially collapsible and radially expandable ring.

In FIG. 11, radiopaque marker 120 is in the form of a complete end ring of stent 200. Radiopaque marker ring 120 includes a plurality of ring struts 122 jointed together by bending elements 124 configured to allow radiopaque marker ring 120 to reduce and expand in diameter in the same manner described above for other rings 20. Radiopaque marker ring 120 and other rings 20 are arranged longitudinally and centered on the same central axis of the stent.

Link struts 22 connect radiopaque marker ring 120 to adjacent ring 20 made of a polymer substrate material. Radiopaque marker ring 120 is made of a substrate material that has a greater radiopacity than the polymer substrate material of ring 20. Each link strut 22 has a single connector 126 which includes bulb 128 and socket 130. Each bulb 128 (first or second portion of connector 128) is integrally formed on radiopaque marker ring 120. Each socket 130 (second or first portion of connector 128) is integrally formed on adjacent ring 20. Bulb 128 is trapped within socket 130 during crimping and expansion of ring 20 and radiopaque marker ring 120.

In other embodiments, the bulb-and-socket arrangement of one or more connectors 126 is reversed such that socket 130 is integrally formed on radiopaque marker ring 120, and corresponding bulb 128 is integrally formed on adjacent ring 20. Additionally, the bulbs and sockets may alternate in orientation from link to link.

Figure 12:
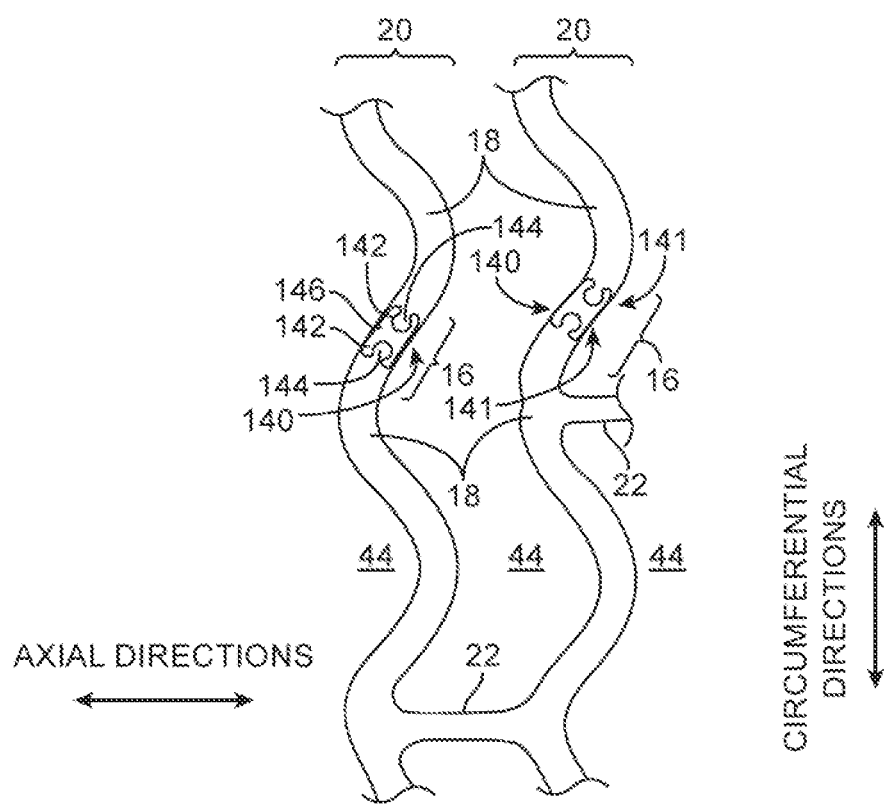
FIG. 12 is a plan view of a portion of a stent in an un-crimped state, showing a radiopaque marker of a ring strut.

In FIG. 12, radiopaque marker 140 is in the form of a ring strut segment. Each radiopaque marker 140 is disposed between bending elements 18. As opposed to radiopaque markers 140, it is bending elements 18 which perform most of the flexing when rings 20 are radially collapsed and expanded in diameter. Each radiopaque marker 140 is retained by two connectors 141 spaced apart from each other. Each connector 141 is in the form of a bulb-and-socket arrangement and comprises hooked fingers 142 and knob 144. Each hooked finger 142 is integrally formed on radiopaque marker 140. Each knob 144 is integrally formed on ring 20 and functions as a retainer for securing radiopaque marker 140. Knob 144 is trapped between hooked fingers 142 during crimping and expansion of rings 20.

Radiopaque marker 140 includes medial segment 146 between connectors 141 and, more particularly, axially between hooked fingers 142. No substrate material of respective ring 20 extends through or around medial segment 146. A surface coating of material may be applied on top of rings 20 and radiopaque markers 140. Such a coating is not a substrate material of rings 20.

Radiopaque marker 140 divides open spaces 44 on each side of ring 20. With radiopaque marker 140 eliminated, open space 44 axially to the left of ring 20 would merge with open space 44 axially to the right of ring 20. Radiopaque marker 140 is arranged such that its elimination would result in loss of all direct structural connection between circumferentially adjacent bending elements 18 on the same ring. Also, elimination of radiopaque marker 140 would result in a complete structural break in the ring strut 16 from which it is eliminated. It should be understood that each ring 20 extends around in a circle (see, for example FIG. 4D), so even with the elimination of radiopaque marker 140 from ring strut 16 between two bending elements 18 on the same ring, there would still be an indirect structural connection between those two bending elements via a circular route running in directions away from the break in ring strut 16.

FIG. 12 also shows radiopaque marker 140 connecting two ends (bulbs 144) of respective ring 20 such that elimination of radiopaque marker 140 would result in loss of all direct structural connection between the two ends of ring 20.

In other embodiments, the bulb-and-socket arrangement of one or more connectors 141 is reversed in that hook fingers 142 are integrally formed on ring 20, and corresponding knob 144 is integrally formed radiopaque marker 140.

Figure 3:
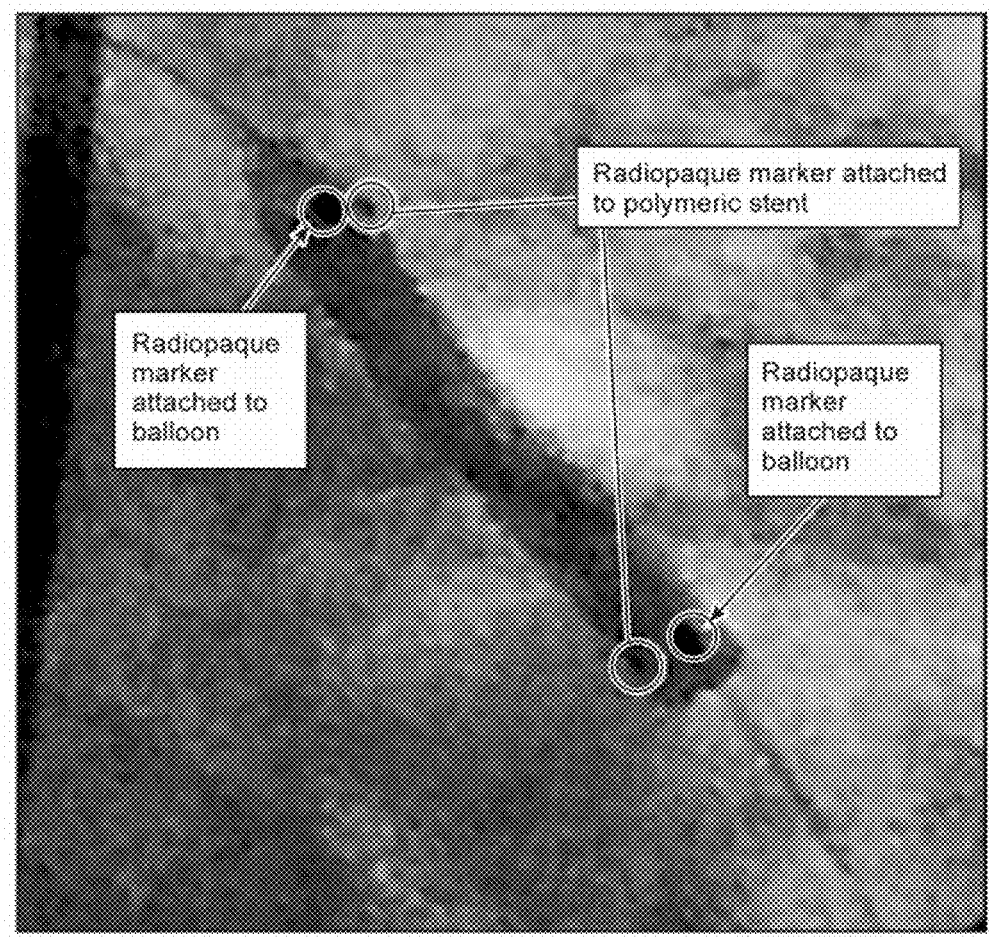
FIG. 3 is an image taken using fluoroscopy, showing the radiopaque markers of FIG. 2 on a stent compared to radiopaque markers on a balloon used to deliver and deploy the stent.

Radiopaque markers 40, 100, 140 described above can be implemented in a multitude of different stent strut patterns, such as the stent strut patterns shown in FIGS. 1 and 5 herein. Examples of other strut patterns that may incorporate radiopaque markers 40, 100, 140 include without limitation the strut patterns described in U.S. Pat. No. 7,476,245; FIG. 3 of U.S. Pat. No. 8,002,817; and U.S. Publication Nos. 2010/0244305 and 2013/0085563.

Radiopaque marker ring 120 can be configured according to any one of a multitude of different ring patterns, such as the ring pattern shown in FIG. 5 herein. For example, radiopaque marker ring 120 can be implemented on one or both end rings 78 in FIG. 5. Examples of other ring patterns for radiopaque marker ring 120 include without limitation the ring patterns described U.S. Pat. No. 8,002,817 and U.S. Publication Nos. 2010/0244305 and 2013/0085563.

Radiopaque markers 40, 100, 120, and 140 can be implemented in combination and in any number on the same stent. For example, multiple radiopaque markers 40 can be implemented with any number of radiopaque markers 100, 120, and 140 on the same stent to form various embodiments.

In the embodiments above, rings 20 and retainers 42 can be made by laser cutting a hollow polymer cylinder which has been radially expanded as described in U.S. Pat. No. 8,002, 817. The hollow polymer cylinder can be made by extruding one or more bioresorbable polymers through a circular die to form a precursor tube consisting essentially of the one or more bioresorbable polymers. The precursor tube may then be heated and radially expanded, such as by introduction of pressurized air into the tube, in order alter the orientation of molecular polymer chains and thereby increase fracture toughness and strength. Some material is then cut away from the radially expanded tube, such as by laser machining. The remaining material is in the form a tubular scaffold comprising rings 20, link struts 22, and retainers 42. With this process, the one or more bioresorbable polymers used during the extrusion step become the polymer substrate material of rings 20, link struts 22, and retainers 42. With this process, the polymer substrate material excludes material which may optionally be applied onto any of rings 20, link struts 22, and retainers 42 after the radial expansion step or after the cutting step.

In the embodiments above, any of radiopaque markers 40, 100, 120, 140 can be laser cut from a flat piece of foil or from a hypotube having the same inner and/or outer diameter as the radially expanded polymer tube from which rings 20, link struts 22, and retainers 42 are made. After a radiopaque marker is formed by cutting, it can be mounted onto retainers 42 by sliding it in a radial direction until its features interlock with features of a retainer on ring 20. The radiopaque marker dimensions may be slightly oversized, or the retaining features slightly undersized, in order to achieve good securement of the marker in the stent. For example, bulb 50 on radiopaque marker 40 can have a slightly larger size than a corresponding cavity 46 of retainer 42. Also, recess 94 in radiopaque marker 40 can be slightly smaller than a corresponding knob 92 on retainer 42.

In any one or more of the embodiments above, rings 20, retainers 42, and strip 90 are made of a biostable polymer substrate material or a bioresorbable polymer substrate material to form various embodiments. In any one or more embodiments above, the bioresorbable polymer material is a material selected from the group consisting of poly(L-lactide) ("PLLA"), poly(L-lactide-co-glycolide) ("PLGA"), poly(D, L-lactide-co-glycolide), poly(L-lactide-co-caprolactone), and poly(L-lactide-co-D-lactide) ("PLLA-co-PDLA"). Examples of polymers for the polymer substrate material include without limitation the polymers described in U.S. Pat. No. 8,002,817.

In any one or more embodiments above, rings 20, retainers 42, and/or strip 90 are not made of metal, and their substrate material consists of or consists essentially of polymer material, consists of or consists essentially of one or more biostable polymer materials, consists of or consists essentially of one or more bioresorbable polymer materials, or consists of or consists essentially of a combination of biostable and bioresorbable polymer materials.

In the embodiments above, radiopaque markers 40, 100, 120, 140 are made of a radiopaque material that has a radiopacity greater than that of the polymer substrate material from which rings 20 are made. In any one or more embodiments above, the radiopaque material is biostable. In any one or more embodiments above, the radiopaque material includes no polymer. In any one or more embodiments above, the radiopaque material either includes metal, consists essentially of metal, or consists of metal. In any one or more embodiments above, the radiopaque material either includes, consists essentially of, or consists of any of platinum and iridium. In any one or more embodiments above, the radiopaque material either includes, consists essentially of, or consists of platinum, iridium, cobalt chromium alloy, stainless steel (316L), high nitrogen stainless steel, Nitinol, tantalum, nickel, tungsten, titanium, gold, magnesium, or an alloy or combination of any two or more thereof. In any one or more embodiments, the radiopaque material may be biodegradable.

Methods for qualitative and quantitative comparison of the radiopacity of radiopaque markers versus that of the polymer substrate material of the stent can be developed with reference to ASTM F640-12, "Standard Test Methods for Determining Radiopacity for Medical Use," which is incorporated herein by reference in its entirety.

Various approaches can be used to qualitatively and/or quantitatively compare the radiopacity of the material from which radiopaque markers 40, 100, 120, 140 are made and the radiopacity of the polymer substrate material from which rings 20, retainers 42, and strip 90 are made. Comparison can be performed by taking a fluoroscopic image. An image can also be taken using an X-ray film or by other radiographic methods. The fluoroscopic image, X-ray image, or radiographic image (hereinafter "image") can be taken of the radiopaque marker and polymer substrate, individually or while radiopaque marker is mounted on a portion of the polymer substrate. The intensity level at an area on the image corresponding to the radiopaque marker can be compared against the intensity level of another area on the image corresponding to the polymer substrate material located away from the radiopaque marker. For example, the level of intensity can correspond to gray level, and a more radiopaque structure may appear darker than a less radiopaque structure. If the image is in the form of a negative image, a more radiopaque structure may appear lighter or whiter than a less radiopaque structure. A qualitative comparison of the level of intensity can be performed by human visual inspection of the image.

In addition or alternatively, a quantitative comparison of the level of intensity can be performed by inputting the image to a densitometer or to a digital analysis program. The densitometer can provide a measurement of optical densities at an area on the image corresponding to the radiopaque marker and another area on the image corresponding to the polymer substrate material located away from the radiopaque marker. A digital analysis program can provide a measurement of pixel densities from multiple points (subsequently averaged) at an area on the image corresponding to the radiopaque marker and another area on the image corresponding to the polymer substrate material located away from the radiopaque marker. In addition, radiopacity can be quantified according to the Hounsfield scale, which is based on the attenuation coefficients of distilled water and air. Distilled water is defined at 0 Hounsfield units (HU=0) while air is defined at HU=−1000. Materials that are more radiopaque than water will have an HU value>0. Indicative values are: muscle has HU=+40, bone has HU>400 and up to +3000, and very dense metals have HU=+4000.

In some embodiments, the ratio of HU value of radiopaque markers 40, 100, 120, 140 to HU value of polymer rings 20 is at least 10:1, at least 20:1, at least 40:1, at least 50:1, or at least 100:1. A greater ratio provides increased contrast in the image between the radiopaque markers and the polymer ring.

A surface coating containing a therapeutic agent, a polymer, solvent, or a combination thereof, can be applied on the polymer substrate material of any of rings 20, retainers 42, and strip 90 before or after the radiopaque marker 40, 100, 120, 140 is attached to ring 20, retainers 42, or strip 90. The surface coating can also be applied to the radiopaque marker 40, 100, 120, 140. Therapeutic agents include without limitation drugs and substances that, when administered in therapeutically effective amounts, have a therapeutic beneficial effect on the health and well-being of the patient or subject. Therapeutic agents include without limitation an anti-proliferative, anti-inflammatory or immune modulating, anti-migratory, anti-thrombotic or other pro-healing agent or a combination of two or more thereof. Therapeutic agents include without limitation those described in U.S. Publication Nos. 2010/0244305. Polymers include without limitation those described in U.S. Pat. No. 8,002,817.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An implantable stent comprising:
a first ring and a second ring, each of which is configured to radially expand and is made of a polymer substrate material; and
a radiopaque marker made of a material having a radiopacity greater than that of the polymer substrate material, wherein the radiopaque marker
connects a first portion of the first ring to a second portion of the second ring such that elimination of the radiopaque marker results in loss of all direct structural connection between the first portion and the second portion,
wherein a first retainer is integrally formed on the first ring, a second retainer is integrally formed on the second ring, and the first and second retainers are configured to mate with and retain respective opposite ends of the radiopaque marker,
wherein a mated portion of the respective opposite ends of the radiopaque marker is entirely in contact with sidewalls of the respective first and second retainers.

2. The implantable stent of claim 1, wherein each of the first ring and the second ring comprises a plurality of ring struts connected to each other by bending elements, the radiopaque marker forms part or all of a link strut that directly connects a first bending element of the first ring to a second bending element of the second ring, and elimination of the radiopaque marker results in loss of all direct structural connection between the first bending element and the second bending element.

3. The implantable stent of claim 1, wherein a bulb is integrally formed on the radiopaque marker, either the first retainer or the second retainer includes a cavity configured to keep the bulb trapped within the cavity while the first and second rings are radially expanded.

4. The implantable stent of claim 1, wherein a knob is integrally formed on either the first retainer or the second retainer, and the radiopaque marker includes a recess configured to keep the knob trapped within the recess while the first and second rings are radially expanded.

5. The implantable stent of claim 1, wherein the first retainer protrudes out from the first ring in a direction away from the second ring, and the second retainer protrudes out from the second ring in a direction toward the first ring.

6. The implantable stent of claim 1, wherein the first ring is configured to be crimped from an un-crimped state to a crimped state, an empty axial space exists between the first ring and the radiopaque marker when the first ring is in the un-crimped state, and the empty axial space is reduced or eliminated when the first ring is in the crimped state.

7. The implantable stent of claim 1, wherein the radiopaque marker has a radial thickness that is the same as a radial thickness of the first ring.

8. An implantable stent comprising:
a first ring and a second ring, each of which is configured to radially expand and is made of a polymer substrate material; and
a link strut connecting the first ring to the second ring, the link strut including a radiopaque marker, wherein no polymer substrate material of the first ring and no polymer substrate material of the second ring extends entirely around the radiopaque marker, and wherein the polymer substrate material of the rings extends partially around the radiopaque marker and, wherein the first and second rings comprise sidewalls extending partially around the radiopaque marker and are entirely in contact with the radiopaque marker.

9. An implantable stent comprising:
a first ring and a second ring, each of which is configured to radially expand and is made of a polymer substrate material; and
a link strut connecting the first ring to the second ring, the link strut including a radiopaque marker, wherein no polymer substrate material of the first ring and no polymer substrate material of the second ring extends entirely through the radiopaque marker, wherein the polymer substrate material of the first and second rings extends partially through the radiopaque marker and, wherein the first and second rings comprise sidewalls extending partially through the radiopaque marker and are entirely in contact with the radiopaque marker and the link strut connects the first ring to the second ring such that elimination of the radiopaque marker from the link strut results in a complete structural break of the link strut.

* * * * *